United States Patent [19]

Hall

[11] 3,982,006

[45] Sept. 21, 1976

[54] M-PHENYLENE DIOXAMIC ACID DERIVATIVES

[75] Inventor: Charles M. Hall, Kalamazoo, Mich.

[73] Assignee: The Upjohn Company, Kalamazoo, Mich.

[22] Filed: Oct. 1, 1975

[21] Appl. No.: 618,508

[52] U.S. Cl............................. 424/267; 260/293.77
[51] Int. Cl.².............. C07D 211/94; C07D 211/66
[58] Field of Search................. 260/293.77; 424/267

*Primary Examiner*—Norma S. Milestone
*Attorney, Agent, or Firm*—Martin B. Barancik; Roman Saliwanchik

[57] ABSTRACT

Novel phenyl dioxamic free radicals are useful in the prophylactic treatment of sensitized humans and animals for allergy and anaphylactic reactions of a reagin or non-reagin mediated nature.

11 Claims, No Drawings

M-PHENYLENE DIOXAMIC ACID DERIVATIVES

BRIEF DESCRIPTION OF THE INVENTION

It has now been discovered that novel compounds of Formula I are useful in the prophylactic treatment of sensitized humans and animals for allergy and anaphylactic reactions of a reagin or non-reagin mediated nature. The compounds are formulated with pharmaceutical carriers for oral, parenteral, inhalation or rectal means of administration.

DETAILED DESCRIPTION OF THE INVENTION

In accordance with this invention there are provided compounds of Formula I, hereafter referred to as Group A

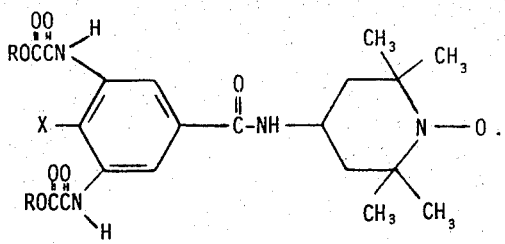

Formula I wherein R is selected from the group consisting of hydrogen, alkyl of one to eight carbon atoms, inclusive,

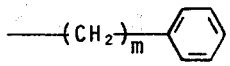

wherein $m$ is 1 or 2, and a physiologically acceptable metal or amine cation;

X is selected from the group consisting of hydrogen, methyl, fluoro, chloro, and bromo.

A still further group of compounds are the compounds of Group A wherein R is selected from the group consisting of hydrogen, alkyl of one to four carbon atoms and a physiologically acceptable metal or amine cation.

Another aspect of the invention is the intermediate generic series of compounds of Formula II,

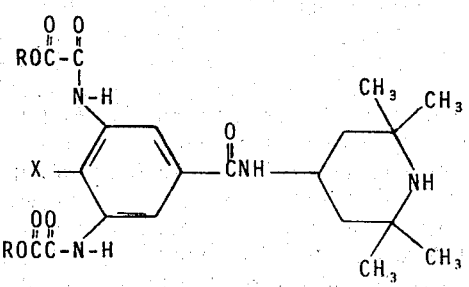

Formula II and their physiologically acceptable acid addition salts, X and R being defined as in Group A. These compounds have anti-allergy activity as well as being useful as intermediates to the final product.

The preferred compound is disodio N,N'-[5-[(2,2-6,6-tetramethyl-1-oxyl-4-piperidyl)carbamoyl]-m-phenylene]-dioxamate of Formula I.

As employed in the above disclosure and throughout the specification and claims, the phrase "alkyl of one to eight carbon atoms, inclusive" includes methyl, ethyl, propyl, butyl, pentyl, hexyl, heptyl, octyl and isomers thereof. Illustrative examples of isomers are isopropyl, tert-butyl, neopentyl, 2,2-dimethylbutyl, isoheptyl and 2,2,4-trimethylpentyl. Alkyls of lesser carbon atom limitation are interpreted similarly.

The phrase "physiologically acceptable amine salt" refers to amines which are accepted by mammals in an essentially non-toxic manner when administered to mammals in conjunction with the acid moiety of the invention. Illustrative of the amines are those derived from primary, secondary or tertiary amines. Examples of suitable amines are methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, adamantylamines, and like aliphatic, cycloaliphatic, and araliphatic amines containing up to and including about eighteen carbon atoms as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-1-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglucamine, N-methylglucosamine, ephedrine, phenylephrine, epinephrine, procaine, and the like. Also included within the amine scope are quaternary amines such as ammonium, tetramethylammonium, tetraethylammonium, benzyltrimethylammonium, phenyltriethylammonium, and the like.

The term "physiologically acceptable metal" includes alkali metals such as sodium and potassium, alkaline earth metals such as calcium and magnesium, and other acceptable metals such as aluminum.

Examples of physiologically acceptable acid addition salts are hydrochloric, sulfuric, phosphoric, palmitic, salicyclic, acetic, cyclohexanesulfamic and like acid addition salts of the compound of Formula II.

The compounds of this invention are readily prepared by methods known to the art. For example, an appropriately X-substituted 3,5-dinitrobenzoyl halide, preferably chloride, is reacted with 4-amino-2,2,6,6-tetramethylpiperidine to give N-(2,2,6,6-tetramethyl-4-piperidyl)-3,5-dinitrobenzamide hydrohalide. The acid addition salt is then converted to the free base by standard reagents. The dinitrobenzamide free base is reduced to the diaminobenzamide by standard reagents. The diaminobenzamide is then converted to the dioxamate by reacting with an alkyl oxalyl halide, preferably ethyl oxalyl chloride, in a suitable base and solvent, or alternatively reacting the diaminobenzamide with a dialkyl oxalate, preferably diethyl oxalate in neat solution or with an additional solvent if necessary at a temperature ranging from about 25°C. to the reflux temperature of the system. The resulting dioxamate is then converted to a metal salt by the addition of a metal hydroxide, and the compound oxidized to the oxyl with an appropriate oxidizing agent.

Solvents useful in the formation of the dinitrobenzamide are inert organic materials such as pyridine, or benzene, or tetrahydrofuran, with an organic base such as triethylamine.

A solution of both reactants is not necessary. One of the reactants may be in a slurry.

Conversion of the acid addition salt to the free base is carried out by adding an equivalent of base to the benzamide.

The reduction of the dinitrobenazmide free base to the diaminobenzamide can be easily effected by catalytic means such as Raney Nickel, palladium on charcoal, or platinum, in the presence of hydrogen. Additionally, chemical means are also available for reduction of nitro to amino, for example, stannous chloride in concentrated hydrochloric acid, and iron in acetic acid with ethanol.

In order to form the dioxamate, the diaminobenzamide is reacted with an alkyl oxalyl halide or dialkyl oxalate. When using an alkyl oxalyl halide, reaction is carried out in base and solvent at standard conditions. Examples of suitable solvents are dimethylformamide, dioxane, and tetrahydrofuran. Appropriate bases include triethylamine, N-methylmorpholine, dimethylpiperazine, and N-methylpiperidine. When the dialkyl oxalate is employed, the starting material is heated together with the dialkyl oxalate or an additional solvent such as a xylene or diphenyl ether if desired, thereby forming the dioxamate. The temperature is from about 25°C. to the reflux temperature of the system.

The metal salt is prepared from the dioxamate by the standard techniques.

The metal salt is oxidized to the desired oxyl compound by standard oxidizing agents and the conditions employed in the art, see Example 1. The metal salt of the free radical can be converted to the free acid which in turn can be esterified to the appropriate ester moiety or converted to the amine cation.

Following are illustrative examples of compounds of the invention. These compounds are intended to exemplify, not to restrict the inventive concept.

TABLE I

| R | X |
| --- | --- |
| H | $CH_3$ |
| $CH_3$ | F |
| $C_3H_7$ | Cl |
| t-$C_4H_9$ | H |
| t-$C_5H_{11}$ | Br |
| $C_6H_{13}$ | H |
| i-$C_7H_{15}$ | Cl |
| 2,2,4-trimethylpentyl | Br |
| $Na^+$ | $CH_3$ |
| $K^+$ | F |
| $Ca^{++}$ | H |
| $NH_4^+$ | F |
| 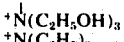 | |
| $^+N(C_2H_5OH)_3$ | Br |
| $^+N(C_2H_5)_3$ | $CH_3$ |
| 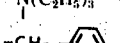 | H |
| 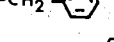 | Cl |

Following are additional specific examples of the invention:

Example 1

N,N'-[5-[(2,2,6,6-tetramethyl-1-oxyl-4-piperidyl)carbamoyl]-m-phenylene]dioxamic acid a. N-(2,2,6,6-tetramethyl-4-piperidyl)-3,5-dinitrobenzamide hydrochloride 4-Amino-2,2,6,6-tetramethyl piperidine (1.7 g.) is added slowly at room temperature to a suspension of 3,5-dinitrobenzoyl chloride (2.5 g.) in pyridine (25 ml.) with stirring. The reaction mixture is stirred at room temperature for eighteen hours during which time a tan solid precipitates. The solid is collected by filtration and recrystallized from water (50 ml.) (4.5 g., m.p. 310° (dec.)). Recrystallization from methanol gives a pure product (2.15 g., m.p. 320° (dec.), 51% yield).

Analysis Calc'd for: $C_{16}H_{23}O_5N_4Cl$ C, 49.68; H, 5.99; N, 14.48; Cl, 9.17. Found: C, 49.35; H, 5.96; N, 14.50; Cl, 9.28.

u.v. (MeOH) λMax. (ε): 208 (24,700), 225.5 (broad sh) (21,050), 290 (1,350) mμ

IR (Nujol): NH/OH 3350, 3230, $^+$NH 3060 (b), 2780, 2590, 2480, C=O 1665, NH def/C=C/$NO_2$ 1625, 1605, 1595, 1590, 1540, $NO_2$/C-N 1350, 1315, Arom. $NO_2$/other 920, 730, 720cm$^{-1}$ Karl Fisher: 2.8% water b. N-(2,2,6,6-Tetramethyl-4-piperidyl)-3,5-dinitrobenzamide N-(2,2,6,6-Tetramethyl-4-piperidyl)-3,5-dinitrobenzamide hydrochloride (18.5 g.) is dissolved in water (350 ml.) and the pH adjusted to 11 with 1.0N NaOH. A cream colored precipitate forms and is collected by filtration, washed with water and dried (14.1 g., m.p. 220°–222°, 84% yield).

c. 3,5-Diamino-N-(2,2,6,6-tetramethyl-4-piperidyl)-benzamide

N-(2,2,6,6-tetramethyl-4-piperidyl)-3,5-dinitrobenzamide (1.0 g.) is dissolved in ethanol (50 ml.) and 10% palladium on charcoal (.1 g.) is added. The reduction is carried out in a Parr apparatus for 2 hours at 40 psi of hydrogen. The catalyst is removed by filtration, washed with a few ml. of ethanol and the filtrate taken to dryness under reduced pressure leaving a tan solid. Recrystallization from ether gives a cream colored product (6.6 g., m.p. 188°–190°C., 79.6% yield).

d. Diethyl N,N'-[5-[2,2,6,6-tetramethyl-4-piperidyl)-carbamoyl]-m-phenylene]dioxamate hydrochloride Ethyl oxalyl chloride (9.0 g.) is added slowly at 0° to a solution of 3,5-diamino-N-(2,2,6,6-tetramethyl-4-piperidyl)benzamide in dimethylformamide (50 ml.) and triethylamine (6.7 g.) with stirring. The reaction mixture is stirred for 1 hour at 0° and then 18 hours at room temperature. Dilution with ether (500 ml.) gives a yellow precipitate that is collected by filtration, washed with ether and dried (23.48 g.). Recrystallization from water (50 ml.) and then chloroform (500 ml.) gives a white product (13.1 g., m.p. 243°–245°C, 80% yield).

Analysis Calc'd for: $C_{24}H_{35}O_7N_4Cl$ C, 54.69; H, 6.69; N, 10.63; Cl, 6.75. Found (Corrected for 4.04% $H_2O$, 3.14% $CHCl_3$): C, 54.05; H, 6.67; N, 10.53; Cl, 6.34.

u.v. (EtOH) λMax. (ε): 247 (20,600), 265 (sl sh) (17,900), 275 (sl sh), (15,750), 305 (sl sh) (6,260) mμ

IR (Nujol): NH/OH 3320, 3260, $^+$NH 2760, 2650, 2580, 2480, 2460, C=O 1735, 1700, 1650, C=C amide II 1600, 1550, C-O/C-N 1300, 1210cm$^{-1}$, λH$_2$O.

Karl Fisher: 4.04% water.
Melt solvate: 3.14% CHCl$_3$.
nmr (CD$_3$OD): 1.4δ (t, 6H, CH$_2$CH$_3$), 1.5δ (s, 6H, CH$_3$), 1.6δ (s, 6H, CH$_3$), 1.4–2.4δ (complex multiplet, 4H, ring CH), 4.4δ (q, 4H, CH$_2$CH$_3$), 4.8δ (s, broad exchangeables and H$_2$O), 8.0δ (d, 2H, Aromatic H), and 8.3δ (t, 1H, aromatic H), 4.4δ (multiplet

e. Disodio N,N'-[5-[(2,2,6,6-Tetramethyl-4-piperidyl)-carbamoyl]-m-phenylene]dioxamate Diethyl N,N'-[(2,2,6,6-tetramethyl-4-piperidyl)carbamoyl]-m-phenylene]dioxamate (5.0 g.) is stirred for 1 hour at room temperature in 1.0N NaOH (30 ml.). The sodium salt precipitates as a white solid and is collected by filtration, washed with water (3 ml.) and dried (3.1 g., m.p. 325° (d.), 68.3% yield).

Analysis Calc'd for: C$_{20}$H$_{24}$O$_7$N$_4$Na$_2$ C, 50.21; H, 5.06; N, 11.71; Na, 9.61. Found: Corrected for 22.55% H$_2$O C, 50.32; H, 3.14; N, 11.94; Na, 9.53.

nmr (D$_2$O): 1.2δ (s, 6H, CH$_3$), 1.3δ (s, 6H, CH$_3$), 0.9–2.1δ (complex multiplet, 4H, ring H); 7.7δ (d, 2H, aromatic H), 7.9δ (t, 1H, aromatic H) 4.3δ (multiplet, 1H,

f. N,N'-[5-[(2,2,6,6-tetramethyl-1-oxyl-4-piperidyl)-carbamoyl]-m-phenylene]dioxamic acid Sodium tungstate (.04 g.) and (ethylenedinitrilo)tetraacetic acid tetrasodium salt (Versine) (.04 g.) are added to a solution of disodio N,N'-[5-[(2,2,6,6-tetramethyl-4-piperidyl)carbamoyl]-m-phenylene]dioxamate (.5 g.) in 6% hydrogen peroxide (10 ml.) with stirring at room temperature. The reaction mixture is stirred for forty-eight hours at room temperature, then acidified with 3N HCl (1 ml.) to give desired diacid as a tan solid that is collected by filtration, washed with water, with acetone, and dried (.35 g., m.p. 250° (d), 74.5% yield). Thin-layer chromatography [silica gel; isopropyl alcohol, H$_2$O, Cl$_3$CCOOH, conc. NH$_4$OH, (75ml:25ml:5g:25ml)] shows the material to be contaminated with a small amount (2–3%) of the starting material. Attempts at recrystallization from methanol result in decomposition. The product is submitted crude for analysis.

Analysis Calc'd for: C$_{20}$H$_{25}$O$_8$N$_4$ C, 53.45; H, 5.61; N, 12.47. Found (Corrected for 10.07% H$_2$O): C, 49.10; H, 4.30; N, 11.19.

u.v. (H$_2$O) λMax (ε): 242 (23,650), 300 (sl sh) (3,500) mμ

IR (Nujol): H$_2$O/NH 3300, Acid OH 2640, C=O 1700, 1650, C-C/amide 1600, 1500, C-O/C-N other 1350, 1265, 1215cm$^{-1}$ The compositions of the present invention are presented for administration to humans and animals in unit dosage forms, such as tablets, capsules, pills, powders, granules, sterile parenteral solutions or suspensions, eye drops, oral solutions or suspensions, and oil-in-water and water-in-oil emulsions containing suitable quantities of the compound of Formula I. The preferred method of administration is by inhalation into the lung by means of an aerosol liquid or powder for insufflation.

For oral administration, either solid or fluid unit dosage forms can be prepared. For preparing solid compositions such as tablets, the compound of Formula I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophylized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Additionally, a rectal suppository can be employed to deliver the active compound. This dosage form is of particular interest where the mammal cannot be treated conveniently by means of other dosage forms, such as orally or by insufflation, as in the case of young children or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1 to 2.5 Gm.

The preferred compositions are those adapted for inhalation into the lung and containing a compound of the invention which is water-soluble. For treatment of allergic conditions of the nose, such as rhinitis, compositions adapted for contact with nasal linings are preferred.

Compositions for inhalation are of three basic types: 1. a powder mixture preferably micropulverized with particle size preferably from about 1 to about 5 microns; 2. an aqueous solution to be sprayed with a nebulizer; and 3. an aerosol with volatile propellant in a pressurized container.

The powders are quite simply prepared by mixing a compound of the formula with a solid base which is compatible with lung tissue, preferably lactose. The powders are packaged in a device adapted to emit a measured amount of powder when inhaled through the mouth.

Aqueous solutions are prepared by dissolving the compound of the Formula I in water and adding salt to provide an isotonic solution and buffering to a pH compatible with inhalation. The solutions are dispersed in a spray device or nebulizer and sprayed into the mouth while inhaling.

Aerosols are prepared by dissolving a compound of the Formula I in water or ethanol and mixing with a volatile propellant and placing in a pressurized container having a metering valve to release a predetermined amount of material.

The liquefied propellant employed is one which has a boiling point below 65°F. at atmospheric pressure. For use in compositions intended to produce aerosols for medicinal use, the liquefied propellant should be non-toxic. Among the suitable liquefied propellants which may be employed are the lower alkanes containing up to five carbon atoms, such as butane and pentane, or a lower alkyl chloride, such as methyl, ethyl, or propyl chlorides. Further suitable liquefied propellants are the fluorinated and fluorochlorinated lower alkanes such as are sold under the trademarks "Freon" and "Genetron". Mixtures of the above-mentioned propellants may suitably be employed. Examples of these propellants are dichlorodifluoromethane ("Freon 12"), dichlorotetrafluoroethane ("Freon 114"), trichloromonofluoromethane ("Freon 11"), dichloromonofluoromethane ("Freon 21"), monochlorodifluoromethane ("Freon 22"), trichlorotrifluoroethane ("Freon 113"), difluoroethane ("Genatron 142-A") and monochlorotrifluoromethane ("Freon 13").

The term "unit dosage form", as used in the specification and claims, refers to physically discrete units suitable as unitary dosages for human subjects and animals, each unit containing a predetermined quantity of active material calculated to produce the desired therapeutic effect in association with the required pharmaceutical diluent, carrier, or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, wafers, granules, cachets, teaspoonfuls, tablespoonfuls, dropperfuls, ampoules, vials, aerosols with metered discharges, segregated multiples of any of the foregoing, and other forms as herein described.

An effective but non-toxic quantity of the compound is employed in treatment. The dosage of the compound for treatment depends on the route of administration and the potency of the particular compound. A dosage schedule for humans of from about 1 mg. to about 20 mg. of compound in a single dose, administered parenterally or by inhalation in the compositions of this invention, are effective for preventing allergy attacks. More specifically, the single dose is from about 2 to about 10 mg. of compound. The oral and rectal dose is from about 5 to about 50 mg. in a single dose. More specifically, the single dose is from about 10 to about 25 mg. of compound. The dosage to be administered can be repeated up to four times daily. However, when it is necessary to repeat treatment, a preferred dosage schedule reduces the secondary treatment dosage to from about 0.5 percent to about 20 percent of the above dosages, more specifically, from about 1 to about 10 percent of the above dosages. In this manner, a state of allergy prophylaxis can be maintained. The reduced dosage is taken until that dosage no longer provides effective protection. At that time, the larger dosage is repeated, followed by the reduced dosage. An example of such a dosage schedule is the following: An asthmatic individual insufflates 10 mg. of the disodio N,N'-[5-[(2,2,6,6-tetramethyl-1-oxyl-4-piperidyl)carbamoyl]-m-phenylene]dioxamate. Four hours later the individual insufflates 1 mg. of the same compound and every four to six hours thereafter insufflates 1 mg. of the same compound until effective asthma prophylaxis is not provided. The individual then insufflates 10 mg. of the same compound, then reduces the insufflation dosage to 1 mg. 4 to 6 hours later. The dosage schedule continues in this manner.

The administration of the compositions of the present invention to humans and animals provides a method for the prophylactic treatment of allergy or all anaphylactic reactions of a reagin or non-reagin mediated nature. That is to say, these compositions, when administered to a sensitized individual prior to the time that the individual comes into contact with substances (antigens) to which he is allergic, will prevent the allergic reaction which would otherwise occur.

For example, the process can be used for prophylactic treatment of such chronic conditions as bronchial asthma, allergic rhinitis, food allergy, hay fever, urticaria, auto-immune disease, exercise induced asthma, stress induced asthma, systemic anaphylaxis, and bird fancier's disease.

EXAMPLE 2

A lot of 10,000 tablets, each containing 2 mg. of diethyl N,N'-[5-[(2,2,6,6-tetramethyl-4-piperidyl)carbamoyl]-m-phenylene]dioxamate is prepared from the following types and amounts of ingredients:

| | |
|---|---|
| Diethyl N,N'-[5-[(2,2,6,6-tetramethyl-4-piperidyl)-carbamoyl]-m-phenylene]-dioxamate | 20 Gm. |
| Dicalcium phosphate | 1,000 Gm. |
| Methylcellulose, U.S.P. (15 cps) | 60 Gm. |
| Talc | 150 Gm. |
| Corn starch | 200 Gm. |
| Magnesium stearate | 10 Gm. |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in preventing hay fever attacks at a dose of one tablet every four hours.

EXAMPLE 3

One thousand tablets, each containing 5 mg. of diethyl N,N'-[5-[(2,2,6,6-tetramethyl-4-piperidyl)carbamoyl]-m-phenylene]dioxamate are prepared from the following types and amounts of ingredients:

| | |
|---|---|
| Diethyl N,N'-[5-[(2,2,6,6-tetramethyl-4-piperidyl)-carbamoyl]-m-phenylene]dioxamate | 5 Gm. |
| Microcrystalline cellulose NF | 410 Gm. |
| Starch | 100 Gm. |
| Magnesium stearate powder | 3 Gm. |

The ingredients are screened and blended together and pressed into tablets.

The tablets are useful to protect against food allergy at a dose of one tablet before meals.

EXAMPLE 4

A sterile preparation suitable for intramuscular injection and containing 2 mg. of N,N'-[5[(2,2,6,6-tetramethyl-1-oxyl-4-piperidyl)carbamoyl]-m-phenylene]dioxamic acid in each milliliter is prepared from the following ingredients:

| | |
|---|---|
| N,N'-[5-[(2,2,6,6-tetramethyl-1-oxyl-4-piperidyl]carbamoyl]-m-phenylene]dioxamic acid | 2 Gm. |
| Benzyl benzoate | 200 ml. |
| Methylparaben | 1.5 Gm. |
| Propylparaben | 0.5 Gm. |
| Cottonseed oil q.s. | 1,000 ml. |

One milliliter of this sterile preparation is injected for prophylactic treatment of allergic rhinitis.

EXAMPLE 5

Six hundred ml. of an aqueous solution containing 10.0 mg. of the tris(hydroxymethyl)aminomethane (THAM) salt of N,N'-[5-[(2,2,6,6-tetramethyl-1-oxyl-4-piperidyl)carbamoyl]-m-phenylen]dioxamic acid per ml. is prepared as follows:

| | |
|---|---|
| THAM salt of N,N'-[5-[(2,2,6,6-tetramethyl-1-oxyl-4-piperidyl)-carbamoyl]-m-phenylene]dioxamic acid | 6.0 Gm. |
| Sodium chloride | 1.2 Gm. |
| Water for injection q.s. | 600 ml. |

The THAM salt and sodium chloride are dissolved in sufficient water to make 600 ml. and sterile filtered.

The solution is placed in nebulizers designed to deliver 0.25 ml. of solution per spray.

The solution is inhaled into the lungs every four to six hours for prevention of asthmatic attacks.

EXAMPLE 6

A powder mixture consisting of 500 mg. of tris(hydroxymethyl)aminomethane salt of N,N'-[5-[(2,2,6,6-tetramethyl-4-piperidyl)carbamoyl]-m-phenylene]dioxamic acid and sufficient lactose to make five grams of mixture is micropulverized and placed in an insufflator designed to deliver 50 mg. of powder per dose.

The powder is inhaled into the lungs every four to six hours for prevention of asthmatic attacks.

The powder is inhaled intranasally every four hours for prevention of rhinitis.

EXAMPLE 7

Twelve grams of an aerosol composition are prepared from the following ingredients:

| | |
|---|---|
| Disodio N,N'-[5-[(2,2,6,6-tetramethyl-1-oxyl-4-piperidyl)-carbamoyl]-m-phenylene-dioxamate | .50 Gm. |
| Freon 12 | 1.440 Gm. |
| Freon 114 | 2.160 Gm. |
| Water | 7.775 Gm. |
| Sorbitan monoleate | 0.600 Gm. |

The disodium salt is dissolved in the water and chilled to −30°C. and added to the chilled Freons. The twelve grams of compositions are added to a 13 cc plastic coated bottle and capped with a metering valve. The metering valve releases 80 mg. of composition in an aerosol. The aerosol is inhaled every 4 to 7 hours for prevention of asthmatic attacks.

EXAMPLE 8

In individuals who require continual treatment in the Examples 2 through 7, the dosage of the Example is given initially and each succeeding administration of the drug is at 1/50 of the initial dosage. This maintenance dosage is continued until effective allergy prophylaxis is not obtained. The initial dosage of Examples 2 through 7 is then started once more, followed by the maintenance dosages.

EXAMPLE 9

After allowing for the differing solubilities of the compounds and the activity of the particular compound as measured, for example, by the in vivo rat passive cutaneous anaphylaxis assay, a suitable quantity of each of the compounds of Table I is substituted for the active compound in the compositions and uses of Examples 2 through 7. Results showing anti-allergy activity are obtained.

EXAMPLE 10

The rat passive cutaneous anaphylaxis assay is run in the following manner:

Female Sprague-Dawley 250 gm. rats are skinsensitized with rat anti-ovalbumin homocytotropic antibody that is heat labile and has a passive cutaneous analyphylaxis titer of 1:128. After a 72-hour latency period, the animals are challenged i.v. with 4 mg. ovalbumin (OA) + 5 mg. Evans blue dye and the test compound. Thirty minutes later the extravascular bluing that results from antigen antibody combination at the skin site is read. Antibody dilutions are used such that in control animals a 4 mm spot is the lowest detectable spot, and 4 or 5 lower dilutions are used to give a range of antibody in each animal. Four to five animals are used for each variable in the experiment. Percent inhibition of the PCA assay is calculated by comparing the spot scores of treated rats with the spot scores of control rats. The spot score is the total number of detectable spots divided by the number of animals.

The tris(hydroxymethyl)aminomethane salt of N,N'-[5-[(2,2,6,6-tetramethyl-1-oxyl-4-piperidyl)-carbamoyl]-m-phenylene]dioxamic acid is prepared by dissolving the dicarboxylic acid in an equivalent weight of aqueous tris(hydroxymethyl)aminomethane and is tested in the rat passive cutaneous anaphylaxis assay in the above manner.

The inhibitory dose₅₀ for the compound is 0.1 mg./kg. by the intravenous route.

All temperatures in the Examples are in degrees Centigrade. Pharmaceutical formulations of compounds of Formula II are compounded in the same manner as formulations of Formula I compounds.

I claim:
1. A compound of the formula

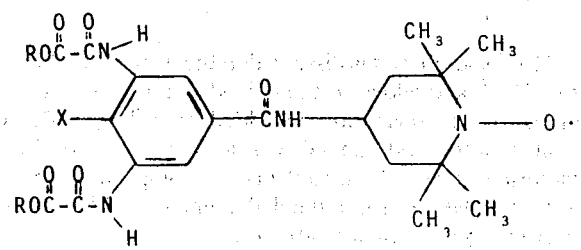

wherein R is selected from the group consisting of hydrogen, alkyl of one to eight carbon atoms, inclusive,

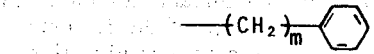

wherein m is 1 or 2 and a physiologically acceptable metal or amine cation;
X is selected from the group consisting of hydrogen, methyl, fluoro, chloro and bromo.

2. A compound in accordance with claim 1 wherein R is selected from the group consisting of hydrogen, alkyl of one to four carbon atoms, inclusive, and a physiologically acceptable metal or amine cation.

3. N,N'-[5-[(2,2,6,6-tetramethyl-1-oxyl-4-piperidyl)-carbamoyl]-m-phenylene]dioxamic acid in accordance with claim 1.

4. Diethyl N,N'-[5-[(2,2,6,6-tetramethyl-1-oxyl-4-piperidyl)carbamoyl]-m-phenylene]dioxamate in accordance with claim 1.

5. Disodio N,N'-[5-[(2,2,6,6-tetramethyl-1-oxyl-4-piperidyl)carbamoyl]-m-phenylene]dioxamate in accordance with claim 1.

6. Ditris(hydroxymethyl)methylamino N,N'-[5-[(2,2,6,6-tetramethyl-1-oxyl-4-piperidyl)carbamoyl]-m-phenylene]dioxamate in accordance with claim 1.

7. A compound of the formula

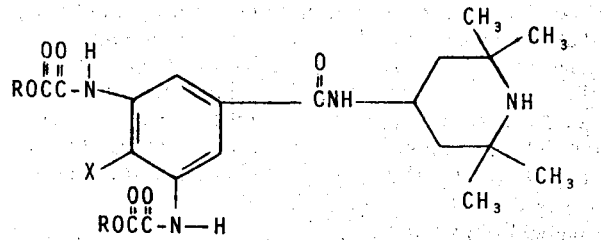

or a physiologically acceptable acid addition salt thereof wherein R is selected from the group consisting of hydrogen, alkyl of one to eight carbon atoms, inclusive,

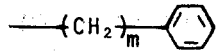

wherein m is 1 or 2 and a physiologically acceptable metal or amine cation;
X is selected from the group consisting of hydrogen, methyl, fluoro, chloro and bromo.

8. Diethyl N,N'-[5-[(2,2,6,6-tetramethyl-4-piperidylcarbamoyl]-m-phenylene]dioxamate hydrochloride in accordance with claim 7.

9. A pharmaceutical composition which comprises an anti-allergy effective amount of a compound of formula

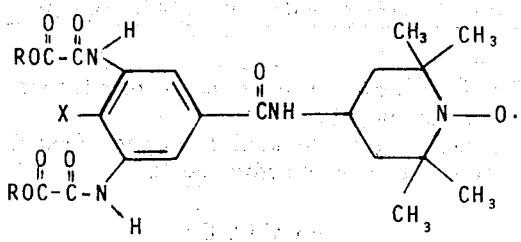

wherein R is selected from the group consisting of hydrogen, alkyl of one to eight carbon atoms, inclusive,

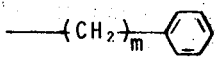

wherein m is 1 or 2, and a physiologically acceptable metal or amine cation;
X is selected from the group consisting of hydrogen, methyl, fluoro, chloro and bromo; in association with a pharmaceutical carrier.

10. A method for the prophylactic treatment of allergy of a reagin or non-reagin mediated nature in a mammal which comprises the administration to the mammal of an antiallergy effective amount of a compound of the formula

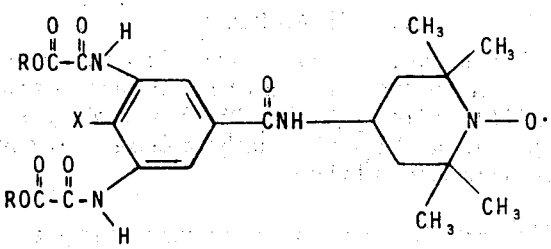

wherein R is selected from the group consisting of hydrogen, alkyl of one to eight carbon atoms, inclusive,

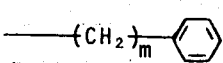

wherein m is 1 or 2 and a physiologically acceptable metal or amine cation;
X is selected from the group consisting of hydrogen, methyl, fluoro, chloro and bromo.

11. A method in accordance with claim 10 wherein the compound is in association with a pharmaceutical carrier.

* * * * *